(12) United States Patent
Burioni et al.

(10) Patent No.: US 7,314,919 B2
(45) Date of Patent: Jan. 1, 2008

(54) HUMAN RECOMBINANT ANTIBODY AGAINST THE HEPATITIS C (HCV) NON STRUCTURAL NS3 PROTEIN NUCLEIC ACID AND USES THEREOF

(75) Inventors: Roberto Burioni, Ancona (IT); Massimo Clementi, Jesi (IT)

(73) Assignee: Biostrands S.r.l., Trieste (IT)

( * ) Notice: Subject to any disclaimer, the term of this patent is extended or adjusted under 35 U.S.C. 154(b) by 0 days.

(21) Appl. No.: 10/480,843

(22) PCT Filed: Jun. 11, 2002

(86) PCT No.: PCT/IT02/00384

§ 371 (c)(1),
(2), (4) Date: Feb. 23, 2004

(87) PCT Pub. No.: WO02/100900

PCT Pub. Date: Dec. 19, 2002

(65) Prior Publication Data

US 2004/0214994 A1 Oct. 28, 2004

(30) Foreign Application Priority Data

Jun. 13, 2001 (IT) .................. RM2001A0336

(51) Int. Cl.
  C07K 16/00 (2006.01)
  C07K 16/08 (2006.01)
  C07K 16/10 (2006.01)
  C07H 21/00 (2006.01)
  A61K 39/00 (2006.01)
  A61K 39/395 (2006.01)
  A61K 39/42 (2006.01)

(52) U.S. Cl. ............... 530/387.1; 530/388.1; 530/389.4; 424/130.1; 424/141.1; 424/149.1; 424/161.1; 536/23.1; 536/23.5; 536/23.53

(58) Field of Classification Search ............. 424/130.1, 424/133.1, 141.1, 142.1, 146.1, 147.1, 149.1; 435/4, 5, 7.1, 7.4; 514/44; 530/350, 387.1, 530/380.15, 383.26, 385.3, 388.1
  See application file for complete search history.

(56) References Cited

U.S. PATENT DOCUMENTS 6,534,064 B1 * 3/2003 O'Hagan et al. ......... 424/205.1

OTHER PUBLICATIONS

Artsaenko et al., Abrogation of hepatits C virus NS3 helicase enzymatic activity by recombinant human antibodies, Journal of General Virology, vol. 84 No. 9, pp. 2323-2332 (Sep. 2003).*
Bretner, Maria, Existing and future therapeutic options for hepatitis C virus infection, Acta Biochimica polonica, vol. 52 No. 1, pp. 57-70 (2005- no date available).*
Daugherty et al., Polymerase chain reaction facilitates the cloning, CDR-grafting, and rapid expression of a muring monoclonal antibody directed against . . . , Nucleic Acids Research, vol. 19 No. 9, pp. 2471-2476 (May 1991).*
Esposito et al., Recombinant human antibodies specific for hepatitis C virus proteins, Archives of Virology, vol. 142 No. 3, pp. 601-610 (Mar. 1997).*
Esposito et al., immunoglobulin kappa light chain, GenPept Accession CAA58108. Feb. 5, 1998.*
Leroux-Roels, Geert, Development of prophylactic and therapeutic vaccines against hepatitis C virus, Expert Review of Vaccines, vol. 4 No. 3, pp. 351-371 (Jun. 2005).*
Lodish et al., Molecular Cell Biology, 3d Ed., Scientific American Books Ins., NY 1995 (no date available).*
Poljak et al., Structure and specificity of antibody molecules, Philosophical Transactions of the Royal Society of London, Series B: Biological Sciences, vol. 272, pp. 43-51 (Nov. 1975).*
Prabhu et al., Inhibition of Hepatitis C Virus Nonstructural Protein, Helicase activity, and Viral Replication by a REcombinant Human Antibody Clone, American Journal of Pathology, vol. 165 No. 4, pp. 1163-1173 (Oct. 2004).*
Rudikoff et al., Single amino acid substitution altering antigen-binding specificity, Proceedings of the National Academy of Sciences, USA, vol. 79, pp. 1979-1983 (Mar. 1982).*
Stocks, Martin, Intrabodies as drug discovery tools and therapeutics, Current Opinion in Chemical Biology, vol. 9 No. 4, pp. 359-365 (Aug. 2005).*
Mondelli et al., Journal of Virology, vol. 68 No. 8, pp. 4829-4836 (Aug. 1994).*
Sullivan et al., Journal of Hepatology, vol. 37 No. 5, pp. 660-668 (2002).*
PCT International Search Report for Biostrands S.R.L., Int'l Application No. PCT/IT02/00384, Filed Jun. 11, 2002, Dated Jul. 3, 2003. [Exhibit 1] .
N. Khalap et al.: "A recombinant human Fab inhibits helicase activity of HCV NS3 and negative strand RNA synthesis." GASTROLOGY, vol. 120, No. 5, Apr. 2001, p. A-8 XP008014494 New York, NY USA abstract 35.
3. N. Khalap et al.: "A recombinant human Fab inhibits helicase activity of HCV NS3 and negative strand RNA synthesis." The Faseb Journal, vol. 15, No. 4, Mar. 7, 2001 p. A-391 XP008014493 Bethesda, MD, USA abstract 322.4.
G. Esposito et al.: "A human antibody specific for hepatitis C virus core protein: synthesis in a bacterial system and characterization." GENE, vol. 164, 1995, pp. 203-209, XP004041876 Amsterdam, The Netherlands abstract figure 5.

(Continued)

*Primary Examiner*—Zachariah Lucas
(74) *Attorney, Agent, or Firm*—Law Offices of Albert Wai-Kit Chan, PLLC

(57) ABSTRACT

An human antibody anti-NS3 protein of the hepatitis C virus (HCV) is described, as will as synthetic and recombinant fragments thereof able to inhibit the helicase activity of the NS3 protein, both in vitro and in vivo, and uses thereof.

7 Claims, 6 Drawing Sheets

OTHER PUBLICATIONS

Figure 1:
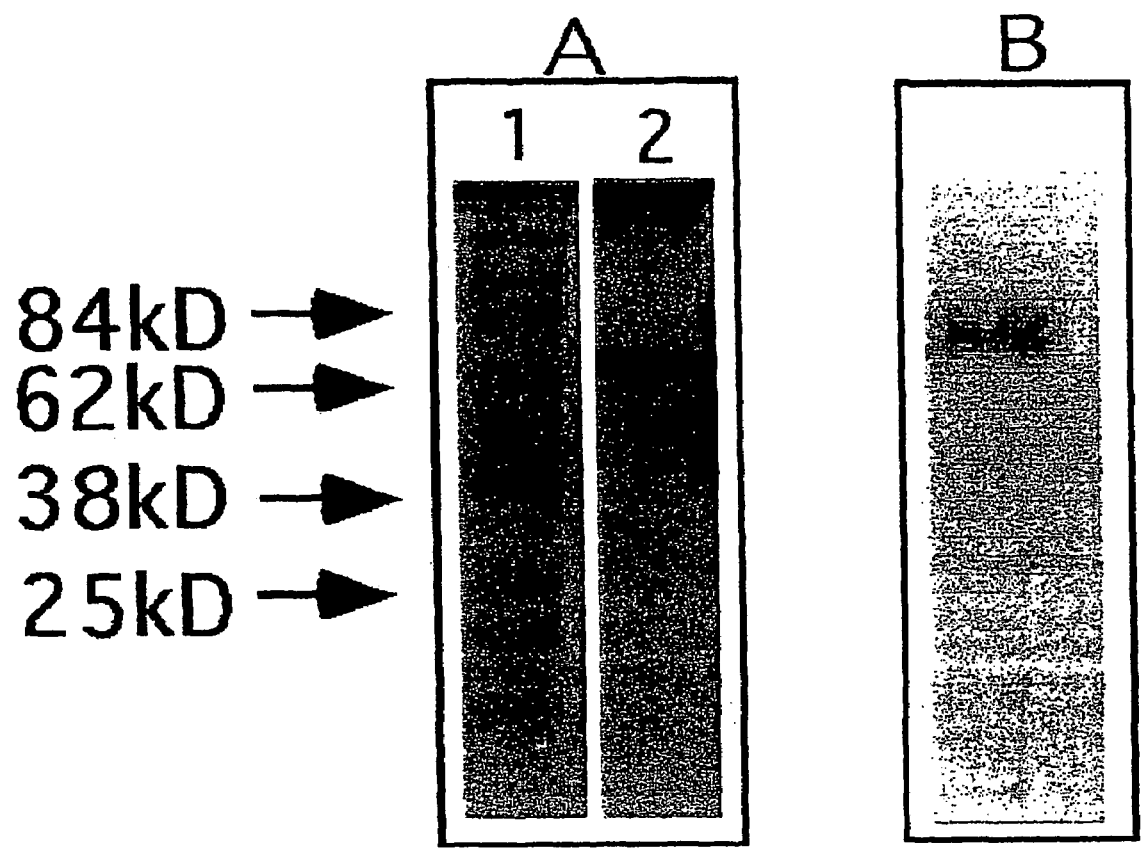

WO 97 12043 A (Chiron Corporation) Apr. 3, 1997 p. 3, line 11—line 12.

T. Heintges et al.: "Cloning, bacterial expression and sequencing of human antibody fragments against hepatitis C virus NS3 by phage display of a recombinatorial phagemid library." HEPATOLOGY, vol. 28, No. 4 part 2, Oct. 1998 p. 287A XP008014496 Baltimore, MD, USA abstract 497.

* cited by examiner

HUMAN RECOMBINANT ANTIBODY AGAINST THE HEPATITIS C (HCV) NON STRUCTURAL NS3 PROTEIN NUCLEIC ACID AND USES THEREOF

The application disclosed herein corresponds to International Application No. PCT/IT02/00384, filed Jun. 11, 2002, which claims priority of Italian Application No. RM2001A000336, filed on Jun. 13, 2001, the contents of which are hereby incorporated by reference into this application.

The invention relates to human recombinant antibodies against the hepatitis C (HCV) non structural NS3 protein, nucleic acids encoding the same and therapeutic and diagnostic uses thereof.

Hepatitis C virus (HCV) infects approximately 4% of the world population (World Health Organization). More than 80% of HCV infected subjects suffer from persistent infection due to the inability to be cleared of the viral agent possibly leading to severe hepatic diseases, as chronic hepatitis, liver cirrhosis and hepatocellular carcinoma (Hoofnagle et al., 1997).

The therapy for chronic infection, based on the combined use of interferon and ribavirin, is extremely expensive and modestly efficient with severe side effects (only one patient of four proves long term results). (Hoofnagle et al., 1994). Viral infection does not provide protecting immunity; this fact, together with extremely high virus variability as to antigenic structure thereof recognized by immune system, currently makes impracticable both efficient serotherapy and provision for vaccines suitable to protect the subjects from the infection. Thus a novel anti-HCV strategy needs to be developed urgently.

NS3 non structural viral protein, exploiting various enzymatic activities (protease, helicase, NTPase), essential for HCV replication (DE Francesco et al., 1998), is a good target for new drugs to be developed. NS3 encoding gene among various viral isolates is relatively conserved, probably because it encodes for a protein which functions cannot be conserved viable in the presence of mutations. Its role is crucial for the virus because if mutated by the same the replication activity is lost.

The authors of the present invention developed human antibodies and active fragments thereof, specific to HCV NS3 protein. From a library derived from HCV chronically infected subject, genes encoding human antibody chains suitable to bind NS3 region with high affinity have been isolated. By insertion of these genes in appositely provided expression vectors, human recombinant antibody fragments (Fab) having high affinity for HCV NS3 protein have been synthesized. Purified preparations of these molecules are able to inhibit in vivo and in vitro remarkably and moderately the HCV NS3 protein helicase and NTPase activities, respectively.

Therefore the molecule is advantageously applied in medicine for anti-HCV therapy. Firstly Fabs, as such, are optimum molecules for some therapy types, by virtue of their short pharmacokinetics and higher ability to penetrate the tissues. The inventive molecule, when inserted within the cells, is able to inhibit the viral replication, therefore making it suitable to antiviral strategies.

In recent years some researchers studied the possibility to interfere in the NS3 by using ribozymes and antisense oligonucleotides has been described in recent years (Wakita, 1994, Alt, 1995, Lieber, 1996). However the virus sensitivity to ribozymes and antisense oligonucleotides is susceptible to remarkable variations due to even minimal sequence modifications.

The inventive molecule or derivatives thereof, when expressed within the cell, could solve the prior art problems. This, however, depends on the availability of the genes encoding for antibodies, suitable to block key proteins for viral replication efficiently and reliably with various viral isolates. The inventive antibody and recombinant derivatives thereof solve these problems.

It is known from prior art the effort to use artificial molecules, as "minibodies" (minimized antibody-like protein), directed against NS3, but this approach failed due to the low affinity of antibody molecules for the antigene (Dimasi et al., 1997).

Recently antiNS3 murine and single strand derived antibodies have been described but this passage decreased the affinity thereof resulting in effectiveness decrease (Zhang et al., 2000).

Therefore not all antiNS3 antibodies are usable. Finally molecules, like this, of murine origin elicit an anti-murine response with unpredictable effects and therefore are not suitable therapeutic tools.

The antibody of the invention, being of human origin, does not suffer from these limitations and, even when in circulation from the death of transfected cells, does not provoke any problem. In addition this characteristic allows to be provided vectors for gene therapy suitable to secrete antibody, thus avoiding its accumulation within the cells resulting in disorders of cell physiology. A secreted antibody, considering the association with endoplasmic reticulum of the viral proteins in the HCV infection, theoretically could be effective against the viral replication without cell damage.

In order to assess this effect the authors constructed an expression vector able to express the antibody in transfected cells. The molecule is produced as a whole human immunoglobulin (identical as those in the blood and tissue of the patient) and is secreted outside of the cell thanks to the presence a "leader" sequence. Due to human origin of the molecule it is not presumable an immune reaction against the same. The authors of the invention described the cloning feasibility of human antibodies against non structural HCV protein and particularly against NS3 (Plaisant et al., 1997). However described antibodies are not able to inhibit enzyme functions as does the inventive one.

Cells wherein the gene encoding for this antibody has been transfected and expressed were tested using an in vitro sophisticated replication system because this virus does not grow in cell culture. According to these methodologies the presence of negative charged RNA chain, a viral replication intermediate, is detected, indicating unambiguously the occurrence of viral replication. For cells wherein the inventive, antibody is expressed as above described, a remarkable inhibition of viral replication, completely kept in the presence of control vectors, is proved.

Therefore the inventive molecule has a remarkable capability to be used in antiviral gene therapy. Cells wherein, using most recent gene delivery techniques, this antibody is expressed should retain unchanged their functions and concurrently do not allow virus replication within themselves. By considering the characteristics of NS3 protein and its ability in inhibiting at the same time two enzyme functions, presumably as other viruses, "escape mutants" hardly appear and associate to viral replication ability which in many cases goes with a loss of virulence.

Availability of this molecule allows a gene therapy for chronic and HCV derived hepatitis to be carried out.

It is therefore an object of the present invention a human antibody against the NS3 protein of the hepatitis C virus (HCV) and recombinant or synthetic fragments thereof able to inhibit in vitro and in vivo helicase activity of NS3 protein. Preferably human anti-NS3 protein antibody is able to recognize the NS3 fragment from aa. 1192 to aa. 1457 of the HCV polyprotein. More preferably the sequence of the variable portion of light chain thereof is as follows:

```
                                              (SEQ ID NO 1)
5'-AELTQSPSSLSASVGDRVTITCRASQGISRYLAWFQQRPGKAPKSL

IYAASHLQSGVPSRFSASGSGTEFTLSISSLQPEDFATYYCQQYDTYPYT

FGQGTKLEIKRTV-3'.
```

It is a further object of the invention a composition for passive immunotherapy comprising in therapeutically effective amounts the inventive antibody.

It is a further object of the invention a nucleic acid encoding for the inventive antibody. Advantageously the nucleic acid can be included in expression vector able to express effectively the inventive antibody. According to a preferred embodiment the recombinant vector also comprises a nucleotide sequence encoding for a signal peptide, essentially contiguous to the sequence encoding for the inventive antibody, able to carry the inventive antibody outside of the cellular environment.

It is a further object of the invention the use for gene therapy of said recombinant vector The invention will be now described by means of explicative, but not limitative, embodiments thereof with reference to the following drawings:

FIG. 1. Purification of the full-length NS3 protein. A His-tagged full-length NS3 protein was purified from *E. coli* using Ni-NTA column. 200 ng of purified protein was run on a 10% SDS-PAGE and stained with Coomassie Brilliant Blue. Lane 1: molecular size marker, lane 2: purified NS3 protein. B. Western blot analysis of the same gel using Rab-aNS3 antibodies.

Figure 2:
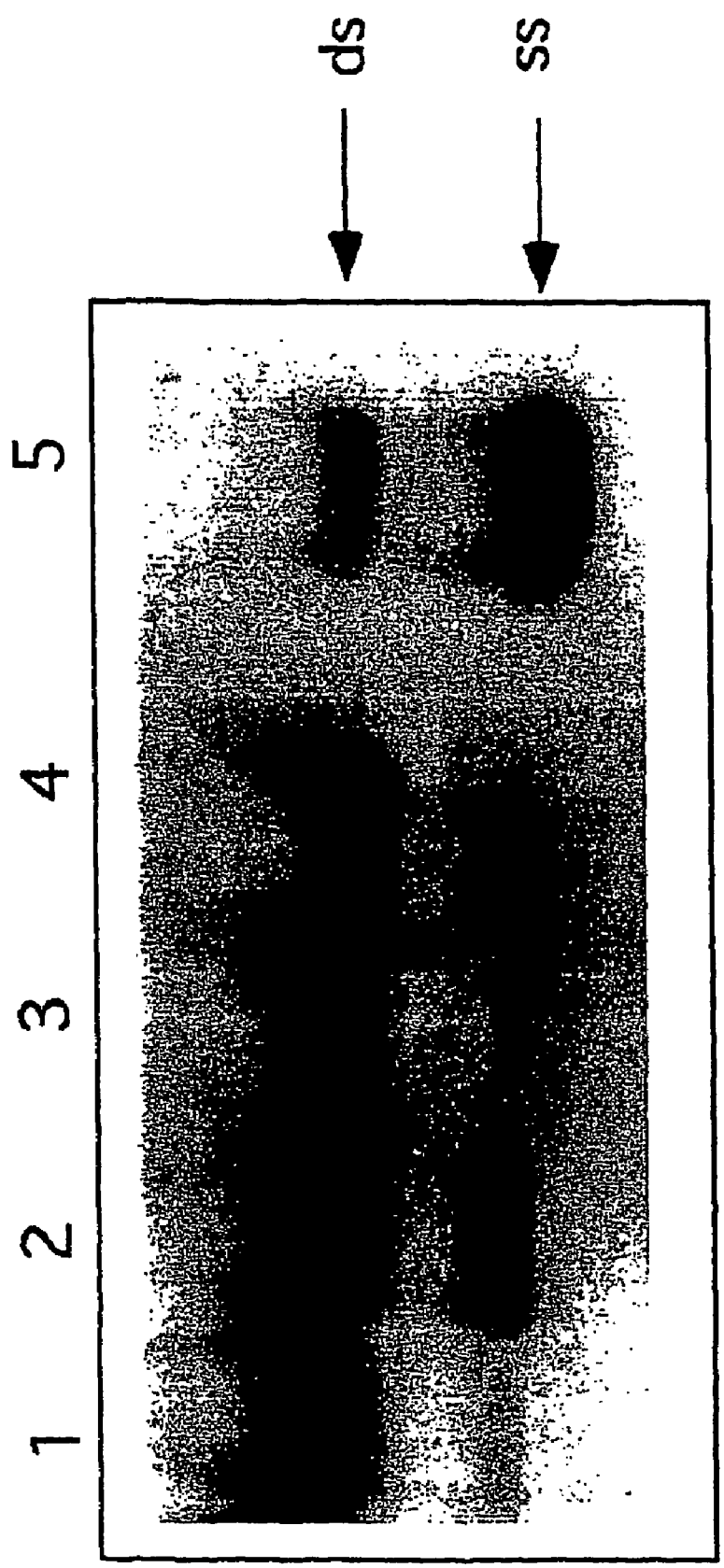

FIG. 2. Helicase activity of purified recombinant full-length NS3 protein. Helicase assay was carried out using radiolabeled partial double strand DNA substrate in the presence of recombinant full-length NS3 protein as described. Lane 1: reaction in the absence of ATP, lane 2: reaction in the presence of 25 nM NS3 protein, lane 3: reaction in the presence of Rab-aNS3 antibody, lane 4: reaction in the presence of anti-E2 antibody and lane 5: reaction mixture denatured by boiling. Helicase activity was abolished in the presence of Rab-aNS3 antibodies and in the absence of ATP.

Figure 3:
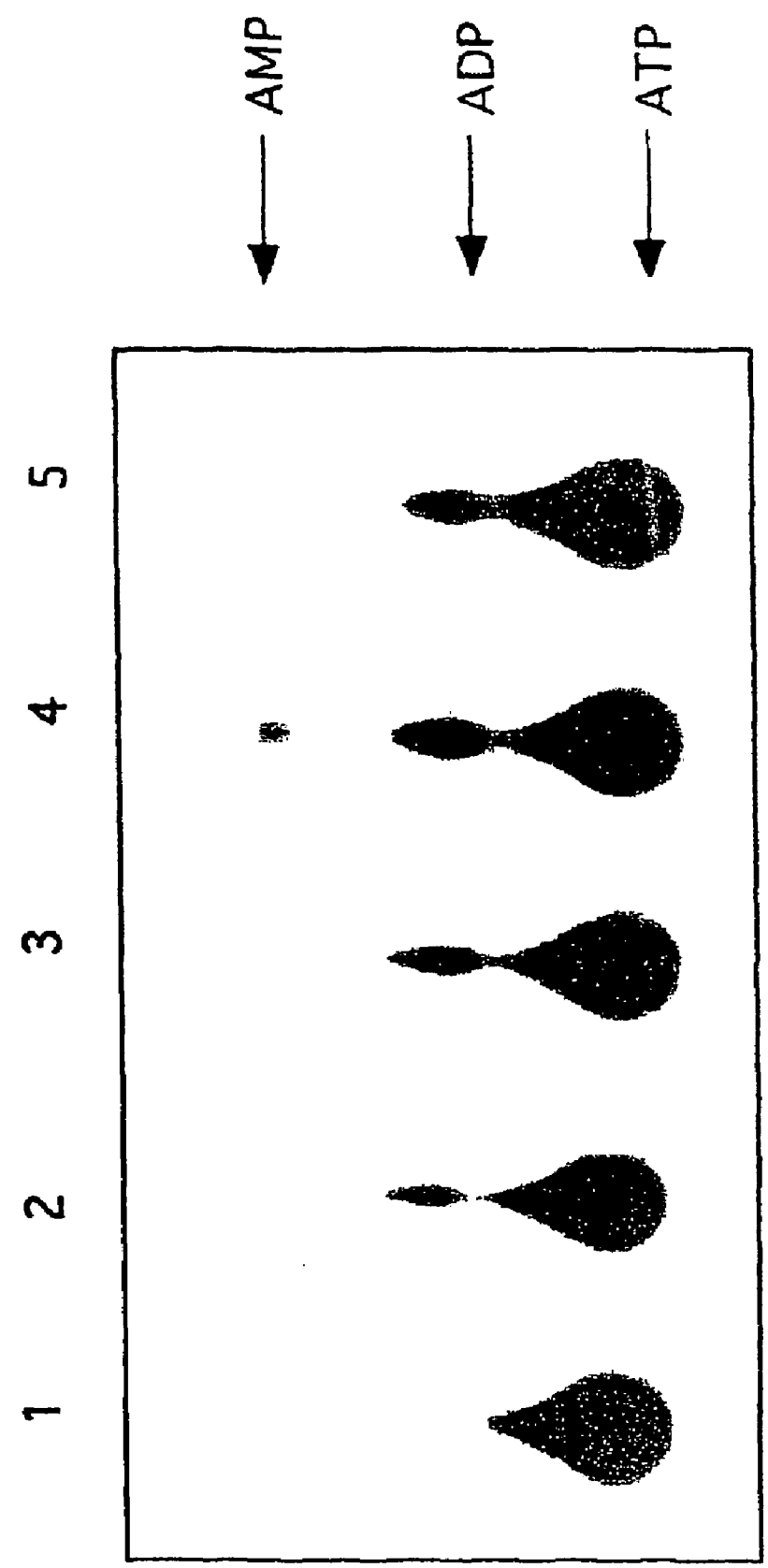

FIG. 3. NTPase activity of recombinant full-length NS3 protein. NTPase assay for NS3 protein was carried out in the presence of NS3 protein and (alfa$^{32}$P)-ATP. Lane 1: reaction in the absence of NS3 protein, lanes 2 to 4: NTPase activity at increasing concentration of 6.0, 12.5 and 25 nM of NS3 protein respectively, lane 5: NTPase assay carried out in the presence of Rab-aNS3 antibodies. NTPase activity is not affected by the presence of Rab-aNS3 antibodies.

Figure 4:
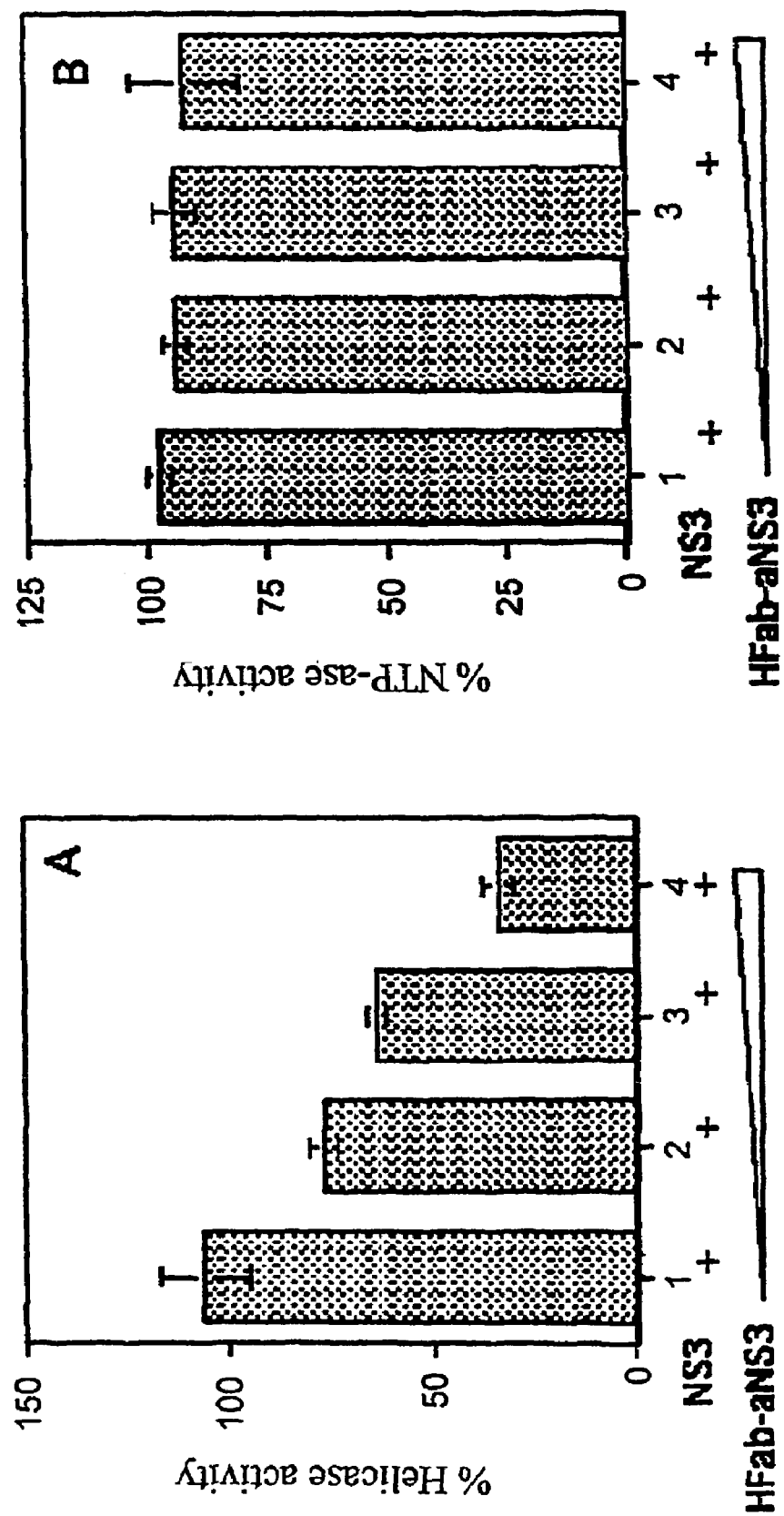

FIG. 4. Human recombinant anti-NS3 (Hfab-aNS3) Fabs inhibit helicase but not NTPase activity of NS3 protein. A inhibition of helicase activity in the presence of 0.87, 1.75, 3.5 and 7 mg/ml HFab-aNS3 (columns 1, 2, 3 and 4 respectively). There is a concentration dependant inhibition of helicase activity of the NS3 protein. B. Inhibition of basal NTPase activity by using 25 nM NS3 protein and the same concentration of HFab-aNS3 as described in 5A. The basal NTPase activity of NS3 protein is not altered significantly by the presence of HFab-aNS3.

Figure 5:
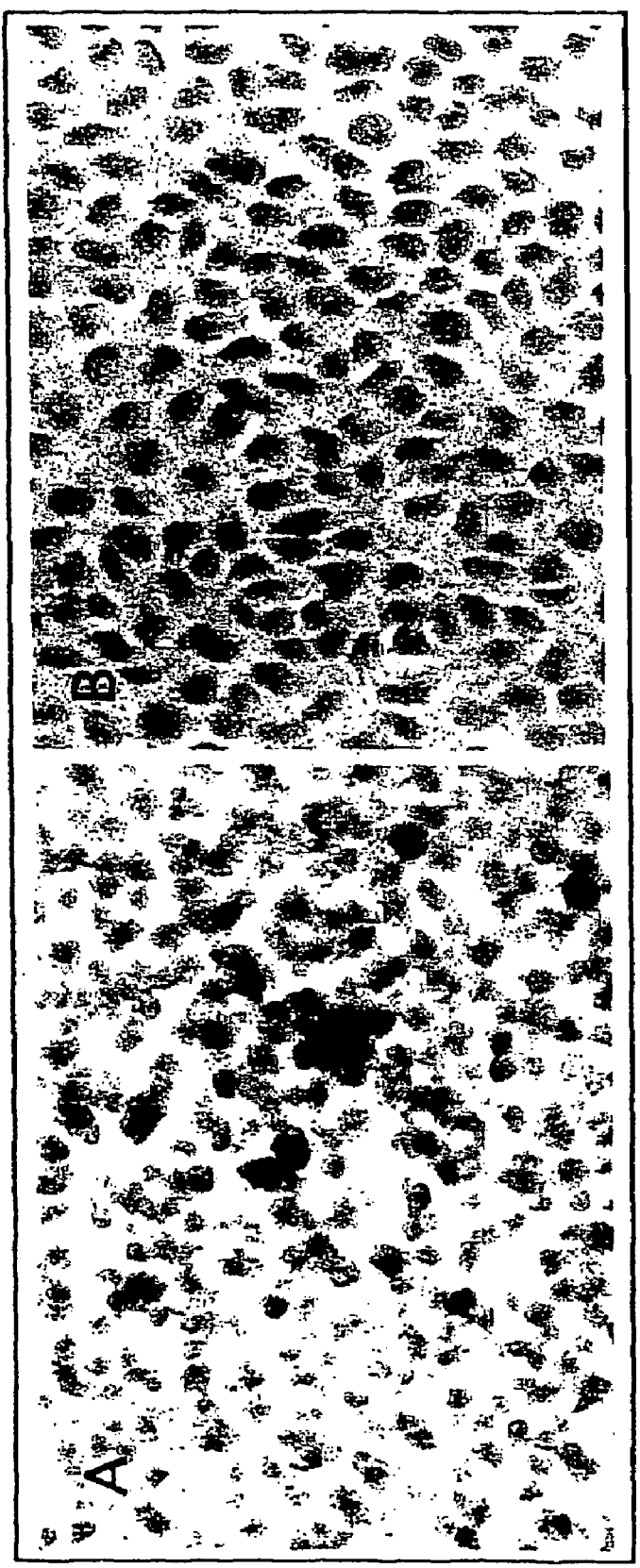

FIG. 5. Intracellular expression of HFab-aNS3. HepG2 cells transfected with pFab-CMV-NS3 were immunostained 48 hours post transfection with peroxidase labelled anti-human Fab antibodies. Prominent brown staining was seen in pFab-CMV-NS3 transfected cells (A) but not in the vector transfected cells (B).

Figure 6:
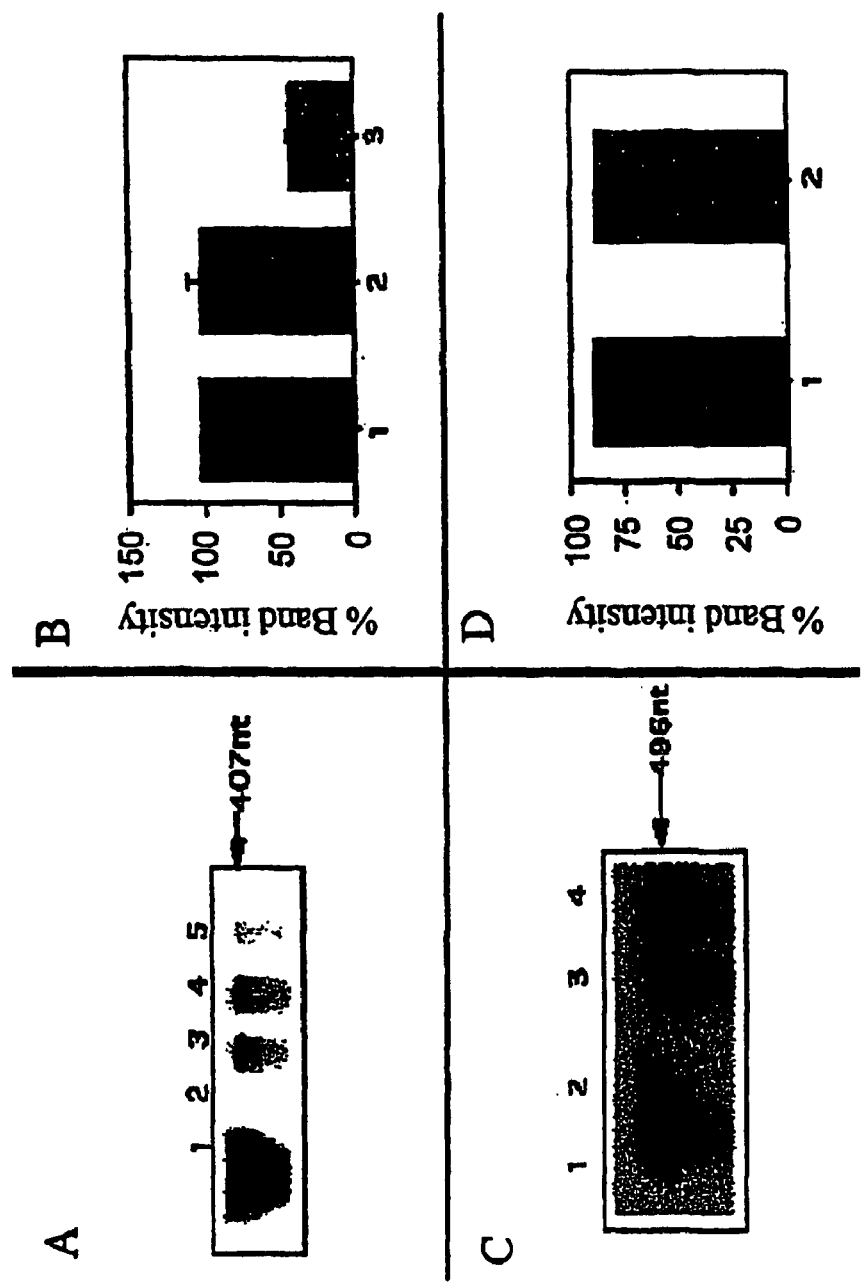

FIG. 6. Anti-viral effect of intracellular expressed HFab-aNS3 in the transfected HepG2 cells. A. RPA assay for detection of HCV negative strand RNA. Lane 1: probe, lane 2: probe digested with RNase, lane 3:, HepG2 cells transfected with pM09.6T7-Rz alone, lane 4: cells cotransfected with pM09.6T7-Rz and pFab CMV (vector control), lane 5: cells cotransfected with pM09.6T7-Rz and pFab-CMV-NS3. B. Quantitation of the protected fragment shows 58.4% reduction of band intensity in the presence of pFab-CMV-NS3. C. RPA assay for detection of GAPDH RNA Lanes 1-3: as in A, lane 4: cells cotransfected with pM09.6T7-Rz and pFab-CMV-NS3.

MATERIALS AND METHODS

Expression and Purification of Recombinant NS3 Protein:

The full-length NS3 coding sequence (from aa 1027 to aa 1657, patent application EP 388232) was PCR amplified from a HCV cDNA clone (pM09.6-T7, 1b genotype) using the following primers:

sense primer 5'TCGCGGATC CGCGCCTATCAGGGC-CTAC 3' (SEQ ID NO 2) and antisense primer 5' GCCG-CAAGCTTGAGTTACGACCTCTA GGTC 3' (SEQ ID NO 3) designed to introduce unique 5' Bam HI and 3' Hind III sites. The NS3 gene was cloned as a BamHI Hind III fragment into pET24d vector (Novagen, Madison, Wis.) to produce pHCV-NS3 recombinant plasmid. *E coli* strain BL21 (DE3) harbouring the pHCV-NS3 was grown at 37° C. until OD$_{600}$ of 0.5 and further incubated in the presence of 4 mM isopropylthiogalactopyranoside (IPTG) at 30° C. for 12 to 18 hours. Bacterial pellets were centrifuged and re-suspended in 50 mM Tris pH7.5, 10% glycerol, 300 mM NaCl and 0.2 mM phenyl methyl sulfonyl fluoride (PMSF), The cells were then sonicated on ice and centrifuged at high speed to separate cell debris. The supernatant was then allowed to flow through the Nickel-charged Ni-NTA column (Novagen, Madison, Wis.), the column was washed with binding buffer (5 mM imidazole, 0.5M NaCl, 20 mM Tris-HCl pH 8.0) and then with washing buffer (40 mM imidazole, 0.5M NaCl, 20 mM tris-HCl pH 8.0). The column bound proteins were eluted with buffer containing 1 M imidazole, 0.5 M NaCl, 20 mM Tris-HCl pH8.0. The eluted fractions were separated by 10% SDS-PAGE, the peak fractions were pooled, dialyzed against 20 mM Tris pH7.5 and 10% glycerol, quantified and stored in aliquots at −20° C. The protein was found to be about 90% pure as by the SDS-PAGE and Western Blot analysis with anti-NS3 antibody (Charlie Rice, Washington University, Saint Louis, Mo.).

Hellcase Assay

The helicase activity of recombinant full-length NS3 protein was measured by extent of unwinding of a partially doubled stranded, radio-labelled substrate. The helicase assay was carried out using previously A partial double-stranded DNA substrate was prepared by annealing two complementary DNA (SEQ ID NO 4)
5-AGAGAGAGAGGUUGAGAGAGAGAGAGUUUGAGAGAGAGAG-3'
(40-mer template strand) and (SEQ ID NO 5)
5'-CAAACUCUCUCUCUCUCAA-CAAAAAA-3'
(26-mer release strand).

The release strand was labelled at the 5'-end with [α-$^{32}$P]-ATP by using T4 polynucleotide kinase (Promega, Madison, Wis.). The two DNA oligonucleofides were combined at a molar ratio of 3:1 (template: release) and annealed by denaturation for 5 minutes at 90° C. followed by slow re-naturation at 23° C. in 20 mM Tris-HCl (pH 8.0), 0.5M NaCl and 1 mM EDTA The partially double-stranded DNA substrate was eluted from 12% PAGE gel using 0.5 M ammonium acetate. The helicase assay was performed in a 15 µl reaction volume containing 50 mM MOPS-NaOH (pH 6.5), 2.5 mM DTT, 100 µg of BSA/ml, 3 mM MgCl$_2$, 1.25-80 nM of the NS3 protein, and 1 nM of DNA substrate. After pre-incubation for 15 minutes at 23° C., 5 mM ATP was added to start the reaction. The reaction was stopped by adding 5 µl of termination buffer (0,1 M Tris pH 7.5, 20 mM EDTA, 0.5% SDS, 0.1% Nonidet P-40, 0.1% bromophenol blue, 0.1% xylene cyanol, and 25% glycerol) after incubation at 37° C. for 30 minutes. An aliquot (8 µl) was analysed on a native 12% polyacrylamide gel containing Tris-borate-EDTA. Strand separation was visualized by autoradiography and quantified using Fuji Film FLA 3000 phosphorimager, NS3 protein and anti-NS3 antibodies or Fab were premixed and incubated at room temperature for one hour. The helicase reaction was then carried out as described. An unrelated Fab directed against lead was used as a control (Dr. D. Blake, Tulane Medical Center LA) Anti NS3 antibodies and anticore antibodies were obtained from Dr. C. Rice University of Washington, St. Louise and Dr. M. Houghton, Chiron Corporation, Emeryville, respectively.

NTPase Assay:

The NTPase activity of the recombinant N83 protein was measured by hydrolysis of [α-$^{32}$P]-ATP according to published protocol (Gallinari et al 1998) using thin layer chromatography (TLC). 10 pmoles of protein, 1 µCi of [α-$^{32}$P]-ATP (300 Ci/mmol, ICN, Costa Mesa, Calif.), 100 µM of ATP, 50 mM Tris-HCl (pH 8.0), 1 mM NaCl and 2.5 mM MgCl$_2$ were mixed in a total volume of 10 µl and incubated at 37° C. for 30 minutes. Reactions were stopped by adding 2 mM EDTA. 1 µl of the reaction mixture was separated using thin layer chromatography and hydrolysis product was quantified by phosphorimager. When reactions were carried out in the presence of antibodies, NS3 protein and antibody were premixed and incubated at room temperature for one hour. Later the NTPase reaction was carried out as described. To confirm the specificity of inhibition by anti-NS3 Fab, an unrelated Fab directed against lead was used in this study as a control.

Development of Recombinant Fab Against HCV NS3 Protein

Human anti-NS3 Fabs were obtained by molecular cloning in a combinatorial phage vector of IgG1/kappa repertoire from a HCV (1b genotype) infected and suffering from chronic hepatitis patient. Preparation of lymphocyte library and the selection of antigen-binding phage was carried out as described by Plaisant et al., 1997 This Fab able to inhibit NS3 helicase activity recognizes amino acid residues 1192 to 1457 thereof. Gene encoding for anti-NS3 Fab was inserted in pComb3 expression vector and used to transform E. coli strain into recombinant Fab source.

Amino acid sequence of the heavy variable chain is as follows:

(SEQ ID 6)
5'LEESGGGLVKPGGSLRLSCVASGLTFSRYNMQWVRQAPGKGLEWVASI

STSGVYIYYADSVTGRFTISRDNSKNSLYLQMNSLGAEDTAVYYCARDLT

FLCGGDCLQPWGQG-3'

Amino acid sequence of the light variable chain is as follows:

(SEQ ID 1)
5'AELTQSPSSLSASVGDRVTITCRASQGISRYLAWFQQRPGKAPKSLIY

AASHLQSGVPSRFSASGSGTEFTLSISSLQPEDFATYYCQQYDTYPYTFG

QGTKLEIKRTV-3'

Purification of recombinant Fab from E coli was carried out using ProteinG-antihuman Fab column as described (Barbas et al 1991). E coli clone carrying the Fab NS3 plasmid was grown in LB medium until an OD$_{600}$ of approximately 1.0 and then overnight at 30° C. in the presence of IPTG (1 mM final concentration), Bacterial pellet was re-suspended in PBS containing 0,5 mM PMSF and then sonicated on ice. The supernatant from high speed centrifugation was further clarified by passing through the 0.22 µm filter (Millipore Corporation, Bedford, Mass.). Resulting supernatant was passed slowly over ProteinG-anti-human-Fab column. The column was prepared according to the protocol (Antibody: a laboratory manual, Harlow and Lane) using ProteinG-sepharose resin (Sigma, St Louis, Mo.) and anti-human IgQ-Fab specific antibodies (Sigma St Louis, Mo.) cross linked with 20 mM Dimethyl Pimelimidate Dihydrochloride (DMP) (Sigma-Aldrich, St Louis, Mo.). The column bound Fab was eluted with 100 mM glycine, pH 2.5 after washing with 30 ml PBS. The fractions were immediately neutralised with Tris 1M (pH 9.0) and concentrated with Centricon 10, MWCO=10.000 (Millipore Corporation, Bedford, Mass.), The purity of the fractions was confirmed by Western Blotting using anti-Fab antibodies.

Western Blot Analysis

The protein samples from eluted fractions or transfected cells were run on 10% SDS-PAGE and electrotransferred to a nitrocellulose membranes (Hybond ECL, Amersham, Ill.). The membrane was blocked with PBS containing 0.1% Tween-20, 3% BSA and 3% non fat dried milk for 1 hour at room temperature. The membrane was then incubated with the primary antibody (1:1000 dilution) for 1 hour at room temperature. After washing with PBS containing 0.1% Tween-20, the membrane was incubated with secondary antibody bound peroxidase(1:1000 dilution) for 1 hour at room temperature. The membranes were developed using chemiluminescence detection system (ECL Western Blotting System, Amersham Pharmacia Biotech, N.J.).

Expression of Fabs in the MepG2 Cells

Plasmid vector pFab CMV (Sanna et al 1999) was used for intracellular expression of human IgG1 derived from anti NS3 Fab fragments. This vector allows expression of light and heavy chains under the control of CMV promoter and, in addition, has convenient restriction sites for cloning from vector pComb3 and can also be used for expression of Fab as IgGi molecules. The SacI-XbaI fragment carrying the light chain and the XhoI-SpeI fragment carrying the heavy chain in vector pComb3 were cloned into the pFab-CMV. The resulting construct was named pFab-CMV-NS3. The expression of Fab molecules in the transfected HepG2 cells was confirmed by immunostaining using anti-serum human anti-Fab antibodies. Immunostaining of HepG2 cells transfected with pFab-CMV-NS3 was carried out 72 hours post-transfection using ABC method (Vectastain, Vector Labs, Burlingame, Calif.). Cells were washed with PBS pH 7.4 twice, dried and fixed with chilled acetone for ten minutes. The cells were then made permeable with 0.05% saponin for 10 minutes at room temperature. Blocking was achieved with 1.5% normal goat serum (Sigma Chemical company, Mo.) and 2% BSA for 30 minutes at room temperature. The cells were incubated with anti-Fab primary antibody (1:500 dilution) overnight at 4° C. After rinsing with PBS, the slides were incubated with biotinylated goat anti-mouse antibody (Santa Cruz, Calif.). Blocking for endogenous biotin and peroxidase was done with 0.9% $H_2O_2$ for 30 minutes followed by Elite avidin-biotin peroxidase complex (VECTOR labs, Calif.). The slides were developed by incubation with diaminobenzidine (DAKO, Calif.) for one minute. Counterstaining was performed with hematoxylin (Sigma chemical company, Mo.) for a minute. The slides were mounted with permount after dehydration, and observed under Olympus optical light microscope.

Cell Culture Virus Infection and DNA Transfection

An inducible cell culture model was used to study efficacy of intracellular expressed Fab to interfere with HCV replication. Cells were infected with a replication defective adenovirus carrying T7 polymerase gene. Later the cells are transfected with a transcription plasmid containing a T7 promoter at the 5' end, full-length cDNA of the HCV genome, a ribozyme sequence from the antigenomic strand of hepatitis delta virus and a T7 terminator. The presence of HCV proteins and formation of HCV negative strand DNA was confirmed.

A human hepatocarcinoma cell line HepG2 (ATCC, N. HB-8065), was grown in MEM containing 10% FBS. These cells were maintained by a regular medium change at 3 days interval. A replication detective adenovirus that expresses T7 RNA polymerase (AdexCAT7) (Aoki et al. 1998; Tatsuo Miyamura, National Institute of Infectious Disease, Tokyo, Japan)) was plaque purified and propagated in human embryonic kidney (293, ATCC N. CRL-1573) cells using standard protocol. Approximately $3 \times 10^6$ cells were plated in 100 mm plates one day before transfection. Cells were infected with AdexCAT7 virus at multiplicity of infection of 10 and after two hours transfected with 10 µg of pM09.6T7Rz (carrying full-length HCV cDNA) with or without 10 µg of pFab CMV NS3 or pFab CMV (negative control) using FuGene6 transfection reagent (Roche Molecular Biology, Indianapolis, Ind.).

Ribonuclease Protection Assay:

To detect negative strand RNA in the transfected HepG2 cells a 407 nt sense probe, specific for NS5A region of HCV RNA, was used. The riboprobe was prepared by in vitro transcription using T7 polymerase and RPA (Ribonuclease Protection Assay) assay was performed using the RPA II kit (Ambion, Austin, Tex.) with slight modifications. Briefly, RNA was extracted from transfected HepG2 cells 2 hours post transfection using standard GITC method. Hybridization was performed in 10 µl after denaturing 10 µg RNA with $10^6$ cpm riboprobe for 3 minutes at 95° C. and then incubated overnight at 45° C. RNase digestion was performed in 100 µl of RNase digestion buffer (10 mM Tris, pH 7.5. 5 mM EDTA, 0.3M NaCl) and 25 U of RNase TI for 30 min at 37° C. Samples were extracted with phenol:chloroform and precipitated with ethanol. The pellet was re-suspended in 8 µl of gel loading buffer, heat denatured and separated on a 8% acrylamide/8M urea gel. The gel was dried and exposed to X-ray film (Kodak X-Omat-AR). Appearance of a 407 bp protected fragment suggested the presence of HCV negative strand in the test RNA Integrity of extracted RNA was confirmed by using a probe for human glyceraldehyde phosphate dehydrogenase (GAPDH), a housekeeping gene in RPA analysis. GAPDH gene, was PCR amplified from culture cells and cloned as HindIII-EcoRV fragment into vector pCDNAS An antisense probe recognizing 496 bp of human GAPDH mRNA was prepared by in vitro transcription as described above and used in RPA analysis, Results Expression and Purification of the Full Length HCV NS3 Protein Full-length NS3 protein was used for all the experiments to be as close to the nature configuration of the NS3 protein as possible. Gene for full-length NS3 protein was cloned from HCV cDNA clone pM09.6T7Rz. Full length NS3 protein was expressed and purified, with an N terminal hexia-histidine tag In E coli. FIG. 1 shows results of NS3 purification and its western blot analysis. Presence of a single band of approximately 67 kDa on SDS-polyacrylamide gel confirmed the homogeneity and, purity of the NS protein (FIG. 1A). To confirm the immunoreactivity of the purified NS3 protein, it was further subjected to Western blotting using anti-NS3 antibody. As depicted in FIG. 1B, a single band of approximately 67 kDa was visualized confirming the specificity and immunoreactivity of the recombinant full-length NS3 protein.

Recombinant NS3 Protein has Helicase and NTPase Activities:

The biological activity of the purified NS3 protein was tested by specific enzyme assays. Results of helicase assay are shown in FIG. 2, In the presence of NS3 protein partial double stranded substrate is converted to single strand as detected by its of higher mobility in acrylamide gel. To confirm that observed is due to NS3 protein, the assay was carried out in the presence of anti NS3 antibody. Helicase activity of NS3 protein was almost completely inhibited by anti-NS3 monoclonal antibodies (FIG. 2). Presence of an anti envelope (HCV E2) antibody did not affect the helicase activity of NS3 (FIG. 2). The helicase activity in absence of ATP did not show any unwinding (FIG. 2) suggesting specificity of the enzyme activity.

NTPase activity exhibited by full-length NS3 protein was studied by standard assay measuring $\alpha^{32}P$-ATP hydrolysis in the presence of different concentrations of NS3 protein. Autoradiography depicted in FIG. 3 shows the presence of degradation products of higher mobility on ascending chromatography. The NTPase activity of NS3 could be directly correlated to the concentration of NS3 protein used in the reaction. The NTPase reaction was carried out with NS3 protein premixed with the anti-NS3 antibody to detect inhibition by the antibody. Surprisingly, in the presence of anti NS3 monoclonal antibody, NTPase activity was not as efficiently inhibited as the helicase activity.

Anti-NS3 Human Fabs Inhibit Helicase and NTPase Activities

Anti-NS3 Fab human fragments purified from *E. coli* were tested for their purity and specificity. Purified Fab fragments are visualized on a denaturing 10% SDS-PAGE as a single band of 25 kDa after comassie blue staining. confirmed by Western blotting using peroxidase labelled anti-Fab human antibodies. A single protein band of 25 kDa size was visualized confirming the authenticity of the purified Fab.

Specific inhibition of helicase and NTPase activities in the presence of different concentrations of purified Fab fragments was studied. The results are shown in FIGS. 4A and 4B. Concentration range of 0.87 mg/ml to 7.0 mg/ml of Fab was mixed with the NS3 protein prior to helicase or NTPase assay. Presence of Fab fragment inhibited the helicase reaction by 54%. The results of NTPase assay carried out in the presence of different concentrations of Fab are as shown in FIG. 4B. About 15% inhibition is detectable for the NTPase activity Both reactions were not affected by addition of a Fab fragment directed against lead in identical conditions confirming the specificity of inhibition by anti NS3 Fab.

Expression of Fab in HepG2 Cells:

In order to verify the ability of anti-NS3 Fab to block helicase activity in vitro following experiments were carried out Ant-NS3 Fabs were expressed in HepG2 cells as entire IgG1 molecules using vector pFab-CMV. The heavy and light chains of the Fab fragments were cloned in the pFab-CMV vector which carries CH2 and CH3 fragments of human IgG1 isotype. The expression of Fabs in the HepG2 cells transfected with pFab CMV NS3 was confirmed by immunostaining of transfected cells. The results are represented in FIG. 5 wherein positive reaction of brown staining in the cytoplasm is evident in the cells transfected by pFab-CMV NS3. The control cells in contrast lack staining completely. These results confirm intracellular expression of Fabs in the transfected HepG2 cells.

Inhibition of Negative Strand Synthesis by Intracellular Expression of Human Anti NS3 IgG:

Effect of intracellularly expressed IgG anti-NS3 on viral replication was studied using an inducible cell culture model. HepG2 cells were infected with replication deficient adenovirus and transfected with the full length HCV cDNA clone with or without pFab-CMV-NS3 or control vector pFab CMV. The RNA was extracted from transfected cells 72 hours post transfection and strand specific RPA was performed to detect HCV negative strand. Presence of 407 bp protected fragment was considered as a positive result. FIG. 6A depicts the results. The presence of a 407 bp protected fragment in the cells transfected with pM09.6T7Rz alone is much more evident as compared than that in cells transfected with both pM09.6T7Rz and pFab-CMV-NS3. These results suggest that there is a significant inhibition of synthesis of negative strand of HCV in the presence of pFab-CMV-NS3. To confirm that the observed result is due RNA degradation, mRNA for a housekeeping gene was detected in both the samples. RPA was carried out for GAPDH mRNA using RNA extracted from cells transfected with and without pFab-CMV-NS3. The results depicted in FIG. 6C, show no difference in the intensity of the protected fragment confirming that the observed difference is not due to RNA degradation.

BIBLIOGRAPHY

World Health Organization (1999) Global surveillance and control of hepatitis C. Report of a WHO Consultation organized in collaboration with the Viral Hepatitis Prevention Board, Antwerp, Belgium, J Viral Hepat 6, 35-47.

Alt, M., Renz, R., Hofschneider, P. H., Paumgartner, G. and Caselmann, W. H. (1995) Specific inhibition of hepatitis C viral gene expression by antisense phosphorothioate oligodeoxynucleotides, Hepatology 22,707-717.

Aoki, Y., Aizaki, H., Shimoike, T., Tani, H., Ishii, K. Saito, L, Matsuura, Y. and Miyamura, T. (1998) A human liver cell line exhibits efficient translation of HCV RNAs produced by a recombinant adenovirus expressing T7 RNA polymerase, Virology 250, 140-150.

Barbas, C. F. d., Kang, A. S., Lemer, R. A. and Benkovic, S. J. (1991) Assembly of combinatorial antibody libraries on phage surfaces: the gene III site, Proc Natl. Acad Sci USA 88, 7978-7982.

De Francesco, R., Pessi, A. and Steinkuhler, C. (1998) The hepatitis C virus NS3 proteinase: structure and function of a zinc-containing serine proteinase, Antivir Ther 3, 99-109.

Dimasi, N., Martin, F., Volpari, C., Brunetti, M., Biasiol, G., Altamura, S., Cortese, R., De Francesco, R., Steinkuhler, C. and Sollazzo, M. (1997) Characterization of engineered hepatitis C virus NS3 protease inhibitors affinity selected from human pancreatic secretory trypsin inhibitor and minibody repertoires, J Virol 71, 7461-7469.

Gallinari, P-, Brennan, D., Nardi, C., Brunetti, M., Tomei, L, Steinkuhler, C. and De Francesco, R. (1998) Multiple enzymatic activities associated with recombinant NS3 protein of hepatitis C virus, J Virol 72, 6758-6769.

Hoofnagle, J. H. (1994) Therapy of acute and chronic viral hepatitis, Adv Intern Med 39, 241-275.

Hoofnagle, J. H. (1997) Hepatitis C: the clinical spectrum of disease, Hepatology 26, 15S-20S.

Lieber, A, He, C. Y., Polyak, S. J., Gretch, D. R., Barr, D. and Kay, M. A. (1996) Elimination of hepatitis C virus RNA in infected human hepatocytes by adenovirus-mediated expression of ribozymes, J Virol 70, 8782-8791.

Plaisant, P., Burioni, R., Manzin, A., Solforosi, L., Candela, M. Gabrielli, A, Fadda, G. and Clementi, M. (1997) Human monoclonal recombinant Fabs specific for HCV antigens obtained by repertoire cloning in phage display combinatorial vectors, Res Viro! 148, 165-169.

Sanna, P. P., Samson, M. E., Moon, J. S., Rozenshteyn, R., De Logu, A., Williamson, R. A. and Burton, D. R. (1999) pFab-CMV, a single vector system for the rapid conversion of recombinant Fabs into whole IgG1 antibodies, Immunotechnology 4, 185-188.

Wakita, T. and Wands, J. R. (1994) Specific inhibition of hepatitis C virus expression by antisense oligodeoxynucleotides. In vitro model for selection of target sequence, J Biol Chem 269, 14205-14210.

Zhang, Z. X., Lazdina, U., Chen, M., Peterson, D. L. and Sallberg, M. (2000) Characterization of a monoclonal antibody and its single-chain antibody fragment recognizing the nucleoside Triphosphatase/Helicase domain of the hepatits C virus nonstructural 3 protein, Clin Diagn Lab Immunol 7, 58-63.

The invention claimed is:

1. An isolated antibody against the NS3 protein of hepatitis C virus (HCV) or recombinant or synthetic fragments thereof able to inhibit helicase activity of the NS3 protein and HCV viral replication having the following sequence of the light chain variable portion: 5'-AELTQSPSSLSAS-VGDRVTITCRASQGISRYLAWFQQR-PGKAPKSLTYAASHLQSGVP SRFSASGSGTEFTL-SISSLQPEDFATYYCQQYDTYPYTFGQGTKLETKRTV-3' (SEQ ID NO: 1); and the following sequence of the heavy chain variable portion: 5' LEESGGGLVKPGGSL-RLSCVASGLTFSRYNMQWVRQAPGK-GLEWVASISTSGVYTYYA DSVTGRFTISRDN-SKNSLYLQMNSLGAEDTAVYYCARDLTFLCGGDCLQPWGQG-3' (SEQ ID NO: 6).

2. The isolated antibody against the NS3 protein of hepatitis C virus (HCV) or recombinant or synthetic fragments thereof according to claim 1, being a human IgG1 molecule.

3. The isolated antibody against the NS3 protein of hepatitis C virus (HCV) or recombinant or synthetic fragments thereof according to claim 1, being an antibody fragment.

4. The isolated antibody against the NS3 protein of hepatitis C virus (HCV) or recombinant or synthetic fragments thereof according to claim 1, being a Fab fragment.

5. A nucleic acid encoding for said antibody according to claim 1.

6. A recombinant vector comprising the nucleic acid as claimed in claim 5 able to effectively express said antibody.

7. A recombinant vector according to claim 6 further comprising nucleotide sequence encoding for a signal peptide essentially contiguous to the sequence encoding for said antibody.

* * * * *

UNITED STATES PATENT AND TRADEMARK OFFICE
CERTIFICATE OF CORRECTION

PATENT NO. : 7,314,919 B2 Page 1 of 1
APPLICATION NO. : 10/480843
DATED : January 1, 2008
INVENTOR(S) : Burioni et al.

It is certified that error appears in the above-identified patent and that said Letters Patent is hereby corrected as shown below:

On Title page item 56 Column 2, line 34, "[Exhibit 1]" should be deleted

On Title page item 57 Column 2, Abstract, "as will as" should be -- as well as --

Column 4, line 34, no space between "C C"

Column 4, line 64, "Hellcase Assay" should be -- Helicase Assay --

Column 4, lines 35-63, the left margin should be lined up with the left margin of line 34

Column 13, line 32, "or" should be -- and --

Column 13, line 37, "PGKAPKSLTYAASHLQSGVP SRFSASGSGTEFTL" should be -- PGKAPKSLTYAASHLQSGVPSRFSASGSGTEFT --

Column 13, line 42, remove space between A and D

Column 13, line 43, "PWGQG-3'" should continue on the next line.

Column 13, line 46, "or" should be -- and --

Column 14, line 31, "or" should be -- and --

Column 14, line 36, "or" should be -- and --

Signed and Sealed this

Sixth Day of May, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 109
<212> TYPE: PRT
<213> ORGANISM: Homo sapiens

<400> SEQUENCE: 1

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Gly Ile Ser Arg Tyr Leu
            20                  25                  30

Ala Trp Phe Gln Gln Arg Pro Gly Lys Ala Pro Lys Ser Leu Ile Tyr
        35                  40                  45

Ala Ala Ser His Leu Gln Ser Gly Val Pro Ser Arg Phe Ser Ala Ser
    50                  55                  60

Gly Ser Gly Thr Glu Phe Thr Leu Ser Ile Ser Ser Leu Gln Pro Glu
65                  70                  75                  80

Asp Phe Ala Thr Tyr Tyr Cys Gln Gln Tyr Asp Thr Tyr Pro Tyr Thr
                85                  90                  95

Phe Gly Gln Gly Thr Lys Leu Glu Ile Lys Arg Thr Val
            100                 105
```

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 2
tcgcggatcc gcgcctatca gggcctac                                    28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 3
gccgcaagct tgagttacga cctctaggtc                                  30

<210> SEQ ID NO 4
<211> LENGTH: 40
<212> TYPE: RNA
<213> ORGANISM: Artificial Sequence
<220> FEATURE:
<223> OTHER INFORMATION: Description of Artificial Sequence:40-mer

<400> SEQUENCE: 4
agagagagag guugagagag agagaguuug agagagagag                       40

<210> SEQ ID NO 5
<211> LENGTH: 26
<212> TYPE: RNA
<213> ORGANISM: Artificial Sequence
<220> FEATURE:
<223> OTHER INFORMATION: Description of Artificial Sequence: 26-mer

<400> SEQUENCE: 5

```
caaacucucu cucucucaac aaaaaa                                         26

<210> SEQ ID NO 6
<211> LENGTH: 112
<212> TYPE: PRT
<213> ORGANISM: Homo sapiens

<400> SEQUENCE: 6

Leu Glu Glu Ser Gly Gly Gly Leu Val Lys Pro Gly Gly Ser Leu Arg
 1               5                  10                  15

Leu Ser Cys Val Ala Ser Gly Leu Thr Phe Ser Arg Tyr Asn Met Gln
            20                  25                  30

Trp Val Arg Gln Ala Pro Gly Lys Gly Leu Glu Trp Val Ala Ser Ile
        35                  40                  45

Ser Thr Ser Gly Val Tyr Ile Tyr Tyr Ala Asp Ser Val Thr Gly Arg
    50                  55                  60

Phe Thr Ile Ser Arg Asp Asn Ser Lys Asn Ser Leu Tyr Leu Gln Met
65                  70                  75                  80

Asn Ser Leu Gly Ala Glu Asp Thr Ala Val Tyr Tyr Cys Ala Arg Asp
                85                  90                  95

Leu Thr Phe Leu Cys Gly Gly Asp Cys Leu Gln Pro Trp Gly Gln Gly
            100                 105                 110
```